US00PP35277P3

(12) United States Plant Patent
Olesen

(10) Patent No.: US PP35,277 P3
(45) Date of Patent: Jul. 25, 2023

(54) ROSE PLANT NAMED 'POULCAS070'

(50) Latin Name: *Rosa hybrida*
Varietal Denomination: Poulcas070

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/803,623

(22) Filed: Sep. 13, 2022

(65) Prior Publication Data

US 2023/0103289 P1 Mar. 30, 2023

(30) Foreign Application Priority Data

Sep. 24, 2021 (QZ) ..... PBR 2021/2365

(51) Int. Cl.
*A01H 5/02* (2018.01)
*A01H 6/74* (2018.01)

(52) U.S. Cl.
USPC ..... Plt./144
CPC ..... *A01H 6/749* (2018.05)

(58) Field of Classification Search
USPC ..... Plt./101, 141, 144
See application file for complete search history.

(56) References Cited

PUBLICATIONS https://www.poulsenroser.dk/de/roses/ShowProduct/53365?productGroup=CAS Retrieved from the Internet on Nov. 17, 2022.*

* cited by examiner

*Primary Examiner* — Susan McCormick Ewoldt

(57) ABSTRACT

A new garden rose plant of the Compact Floribunda class which has abundant, white flowers and attractive foliage. This new and distinct variety has shown to be uniform and stable in the resulting generations from asexual propagation.

2 Drawing Sheets

Botanical designation: *Rosa hybrida.*

Variety denomination: 'Poulcas070'.

This application claims priority to Plant Breeder's Rights Application Number 2021/2365, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulcas070', originated as a single seedling from the stated cross.

The new variety may be distinguished from its male pollen parent and female seed parent primarily by the following characteristics. The male pollen parent plant has a growth height of about 25 cm while the new variety 'Poulcas070' grows to 40 cm in height. The female seed parent plant has single petal white flowers while the new variety has very double, white flowers.

The objective of the hybridization of this rose variety was to create a new and distinct variety with unique qualities, such as:

1. Uniform and abundant white flowers;
2. Vigorous, but compact growth when propagated on its own roots; and
3. Exceptional disease resistance.

This combination of qualities is not present in previously available commercial cultivars of this type, known to the inventor, and distinguish 'Poulcas070' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulcas070' was selected in the spring of 2011 by the inventor as a single plant from the progeny of the aforementioned hybridization.

Asexual reproduction of 'Poulcas070' by rooted cuttings was first done by Mogens N. Olesen in the nursery in Fredensborg, Denmark in July, 2011. This initial and other subsequent asexual propagations conducted in controlled environments have demonstrated that the characteristics of 'Poulcas070' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas070'.

Specifically illustrated in FIG. 1 of the drawings are an open flower viewed from the top, flower petals detached revealing reproductive flower parts, sepals detached revealing the receptacle, and flower buds at various stages of opening.

Figure 1:
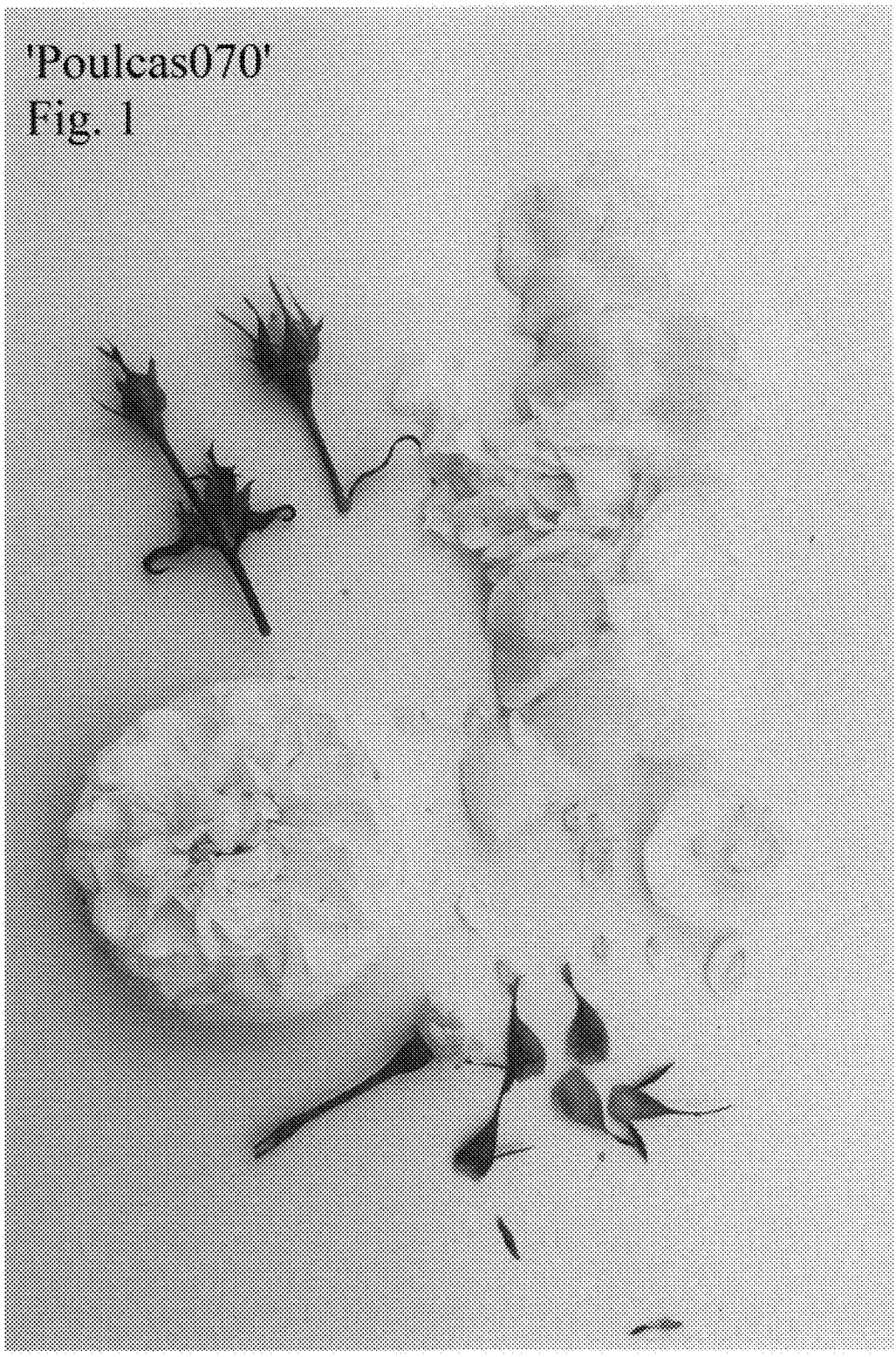
Figure 2:
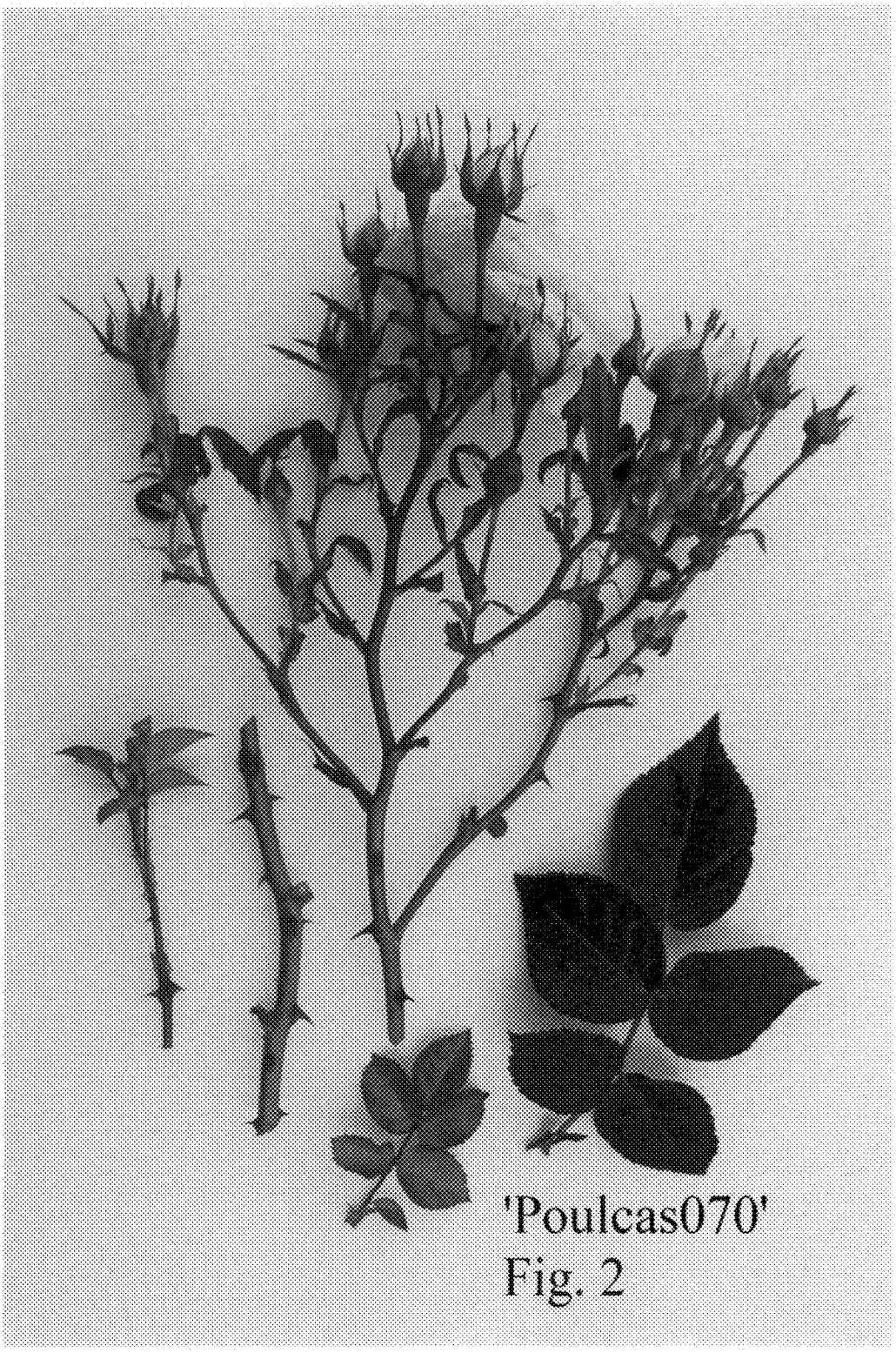

Specifically illustrated in FIG. 2 of the drawings are a cluster of flowers on the branch, mature leaves, mature bare stem revealing prickles, juvenile leaves, and juvenile stems. Plants shown are 2 years of age.

DETAILED DESCRIPTION OF THE VARIETY

The following is a description of 'Poulcas070', as observed in its growth outdoor in Odense Denmark. Observed plants are 18 months of age, and were grown on their own roots in 30 cm containers. Color references are made using The Royal Horticultural Society (London, England) Colour Chart, 2001, except where common terms of color are used.

For a comparison, several physical characteristics of the rose variety 'Poulcas043', U.S. Plant Pat. No. 27,708 are compared to 'Poulcas070' in Chart 1.

CHART 1

| | 'Poulcas070' | 'Poulcas043' |
|---|---|---|
| Petal Count | 80 | 65 |
| Flower Diameter | 85 mm | 70 mm |
| General Tonality of Flower Color | White Group 155B | White Group 155D |

FLOWER AND FLOWER BUD

Blooming habit: Continuous.

Flower bud:

*Size*.—Upon opening, 21 mm in length from base of receptacle to end of bud. Bud diameter is 14 mm.

*Bud form*.—Urceolate.

*Bud color*.—As sepals divide petals are Yellow-White Group 158A with intonations of Red Group 37A.

*Sepal inner surface*.—Color: Yellow-Green Group 146D with intonations of Greyed-Purple Group 183B. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—About 32 mm long, 15 mm wide.

*Receptacle*.—Texture: Smooth. Size: 11 mm in height, 7 mm wide. Color: Yellow-Green Group 144A. Shape: Long campanulate.

*Pedicel*.—Surface: Smooth. Length: 30 mm. Diameter: 3 mm on average. Color: Yellow-Green Group 144A with intonations of Greyed-Orange Group 156B. Strength: Strong.

*Peduncle*.—Length: Varying from 2 to 10 cm. Diameter: About 4 mm. Color: Yellow-Green Group 144A with intonations of Greyed-Orange Group 166B. Texture: Smooth.

Flower bud development: Flower buds are borne in clusters of up to 28 flower buds per flowering branch on average, developing as a thyrse.

Flower bloom:

*Fragrance*.—Strong perfume.

*Duration*.—The blooms have a duration on the plant of approximately 14 days. Petals fall cleanly away from plant after flowers have fully matured.

*Size*.—Flower diameter is about 85 mm when open. Flower depth is 30 mm.

*Flower shape*.—Rosette, very double flowers filled with masses of tiny petals.

*Shape of flower, side view*.—The upper portion is flat convex. The lower portion is concave.

Petalage: Under normal conditions, flowers have about 80 petals.

General tonality of flower: Open flowers are White Group 155B.

Petal color:

*Upon opening, outer petals*.—Upper surface: White Group 155B. Lower surface: White Group 155B.

*Upon opening, inner petals*.—Upper surface: White Group 155B. Lower surface: White Group 155B.

*Basal petal spots, upon opening*.—Upper surface: No distinctive coloration at the petal base. Lower surface: Yellow Group 4B.

*After opening, outer petals*.—Upper surface: White Group 155B. Lower surface: White Group 155B.

*After opening, inner petals*.—Upper surface: White Group 155B. Lower surface: White Group 155B.

*Basal petal spots, after opening*.—Upper surface: No distinctive coloration at the petal base. Lower surface: Yellow Group 4B.

Petals:

*Petal reflex*.—Flat.

*Margin*.—Several clefts 2 or more. Moderate undulations.

*Shape*.—Broad and elliptic. Apex shape: Rounded. Base shape: Acute.

*Size*.—35 mm (l)×41 mm (w).

*Texture*.—Smooth.

*Thickness*.—Average.

Petaloids:

*Size*.—10 mm (l) by 5 mm (w).

*Quantity*.—About 20.

*Shape*.—Elliptical with an acute base and acute apex.

*Color*.—

Reproductive flower parts:

*Pollen*.—None observed.

*Anthers*.—Size: 2 mm in length. Color: Greyed-Yellow Group 160A. Quantity: 33 on average.

*Filaments*.—Color: Yellow Group 4B. Length: 5 mm.

*Pistils*.—Length: 9 mm. Quantity: 25 on average.

*Stigmas*.—Color: Green-White Group 157A.

*Styles*.—Color: Green-White Group 157A.

*Location of stigmas*.—Superior in location relative to the length of the filaments and the height of the anthers.

*Hips*.—None Observed.

PLANT

Plant growth: Upright, bushy. Plants are 40 cm in height, and 40 cm wide.

Stems:

*Color of juvenile growth*.—Yellow-Green Group 144A with intonations of Greyed-Red Group 181B.

*Color of mature growth*.—Yellow-Green Group 146C with intonations of Greyed-Orange Group 166C.

*Length*.—Canes are about 20 cm from the base of the plant to the flowering portion.

*Diameter*.—About 6 mm.

*Internodes*.—On mature canes about 35 to 55 mm between nodes.

*Surface texture*.—Young wood: Smooth. Older wood: Smooth.

Long prickles:

*Incidence*.—9 prickles per 10 cm of stem.

*Size*.—Average length of prickles on mature stems is 10 mm.

*Shape*.—Upper portion is linear. Lower portion is concave.

*Color*.—Juvenile prickles: Greyed-Red Group 180A. Mature prickles: Greyed-Red Group 181A.

Plant foliage:

*Compound leaf*.—160 mm (l)×120 (w).

*Quantity*.—2 leaves per 10 cm of stem on average.

*Leaf bearing angle to the stem*.—45 degrees.

*Color of juvenile foliage*.—Upper side: Yellow-Green Group 144A shaded with intonations of Greyed-Red Group 178A. Lower side: Yellow-Green Group 144A shaded with intonations of Greyed-Red Group 178A.

*Color of mature foliage*.—Upper side: Yellow-Green Group 147A. Lower side: Yellow-Green Group 147B.

Plant leaves and leaflets:

*Stipules*.—Size: 20 mm long, 3 to 4 mm wide. Quantity: 2 per compound leaf. Shape: Linear, slightly broad based with outward extending apex. Margins: Finely serrated. Color: Yellow-Green Group 147A

*Petiole*.—Length: 35 mm. Diameter: 2 mm. Upper surface color: Yellow-Green Group 144A. Lower surface color: Yellow-Green Group 144A.

*Rachis*.—Length: 50 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 70 mm long, 48 mm wide. Shape: Generally Round or cordate. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phraginidium* spp., black spot *Diplocaipon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulcas070' substantially as described and illustrated herein.

* * * * *

'Poulcas070'

'Poulcas070'